United States Patent [19]
George et al.

[11] Patent Number: 5,415,919
[45] Date of Patent: May 16, 1995

[54] TREATING MATERIALS WITH A COMPOUND CONTAINING TIN COVALENTLY BONDED TO A SILYLATING GROUP

[75] Inventors: Billy L. George, Hudson, Wis.; Katherine A. Brown-Wensley, Lake Elmo, Minn.

[73] Assignee: Minnesota Mining and Manufacturing Company, St. Paul, Minn.

[21] Appl. No.: 201,574

[22] Filed: Feb. 25, 1994

Related U.S. Application Data

[63] Continuation-in-part of Ser. No. 808,364, Dec. 16, 1991, Pat. No. 5,316,824.

[51] Int. Cl.$^6$ .................. B05D 1/18; B32B 21/02; D06N 7/04
[52] U.S. Cl. ................... 428/145; 52/516; 427/393.6; 427/420; 427/421; 427/428; 427/430.1; 427/440; 428/141; 428/142; 428/144; 428/340; 428/341; 428/405; 428/406; 428/446; 428/447; 428/516; 428/540; 428/543
[58] Field of Search .............. 52/516; 427/387, 389.7, 427/393, 393.6, 420, 421, 428, 430.1, 440; 428/141, 142, 144, 145, 340, 341, 405, 406, 446, 447, 516, 540, 543

[56] References Cited

U.S. PATENT DOCUMENTS

| | | | |
|---|---|---|---|
| 2,951,770 | 9/1960 | Lodge et al. | 117/100 |
| 3,395,164 | 7/1968 | Leebrick | 260/429.7 |
| 4,080,190 | 3/1978 | Law et al. | 71/67 |
| 4,160,846 | 7/1979 | Strunk et al. | 424/288 |
| 4,260,552 | 4/1981 | Strunk et al. | 260/429 |
| 4,578,489 | 3/1986 | Wehner et al. | 556/100 |
| 4,877,654 | 10/1989 | Wilson | 427/387 |
| 4,999,249 | 3/1991 | Deschler et al. | 428/447 |

FOREIGN PATENT DOCUMENTS

| | | |
|---|---|---|
| 3119643A1 | 12/1982 | Germany . |
| 3828775 | 3/1990 | Germany . |
| 61-233064 | 10/1986 | Japan . |
| 1565882 | 4/1980 | United Kingdom . |

OTHER PUBLICATIONS

"Tributyltin-N,N-dialkyldithiocarbanates as Fungicides for Wood Preservation Against Rot", by J. Kizlink, *JOOCA* 74, No. 9, 1991, pp. 329–330.

"Tin", by G. Wilkinson, F. Stone and E. Abel, *Comprehensive Organometallic Chemistry*, Chpt. 11, vol. 2, pp. 530–535 (1982).

"Silane Coupling Agents", Edwin P. Plueddemann, 2nd Ed., pp. 4–7, 31–37, 238–241 (1991).

Chemical Abstracts, vol. 112, No. 10, Mar. 5, 1990, Columbus Ohio, U.S.

Database WPIL, Week 8319, Derwent Publications Ltd., GB, Apr. 1983: AN 83–45880K and JP,A,58 057 460.

*Primary Examiner*—D. S. Nakarani
*Attorney, Agent, or Firm*—Ramon R. Hoch; Walter N. Kirn; Gary L. Griswold

[57] ABSTRACT

Materials, particularly wood materials and calcium carbonate-containing materials such as concrete and marble, can be protected from the growth of algae by being treated with a compound containing tin covalently bonded to a silylating group such that cleavage of the covalent bonds due to hydrolysis or photolysis is minimized, thus making the treatment ecologically safe. One such compound is $(n\text{-Bu})_3SnCH_2CH_2Si(OEt)_3$. The tin compound can either be incorporated into raw materials from which materials are to be made, or it can be applied to the finished materials. When the tin compound is applied to a material that is algae streaked, the streaking should disappear.

38 Claims, No Drawings

TREATING MATERIALS WITH A COMPOUND CONTAINING TIN COVALENTLY BONDED TO A SILYLATING GROUP

CROSS REFERENCE TO RELATED APPLICATIONS

This application is a continuation-in-part of application Ser. No. 07/808,364, filed Dec. 16, 1991, now U.S. Pat. No. 5,316,824.

BACKGROUND OF THE INVENTION

1. Field of the Invention

The invention is concerned with preserving the aesthetic appearance of architectural and aesthetic structures which are exposed to variable temperatures, moisture/drying cycles, freeze/thaw cycles, acidity variations, and the like, e.g. wood decks, buildings, freestanding walls, statuary, asphalt shingles, and the like. More specifically, the invention concerns the treatment of materials to prevent or remove disfiguring growths such as alga which darkens the materials.

2. Description of the Related Art

Many materials, particularly wood and cement building materials and the coatings thereon, may be subject both to freezing and extreme heat, or to repeated freeze/thaw cycles, which can embrittle, crack, or otherwise degrade the coatings. In other applications, building materials may be subject to high temperatures, as high as 130° F. (54° C.) on an asphalt shingle roof in the southern United States, and thermal degradation may result. Building materials are also exposed to ultraviolet light, which is well known to degrade many materials, and often subjected to repeated rinsing with water, perhaps pH as low as 4.0 ("acid rain"), and evaporative cooling. Building materials are subject to the abrasive action of wind and wind-borne particulates. Other contaminants, some of which may also be nutrients for algae, may also be present, such as calcium carbonate, dirt, oil, or plant material adhered to foundation blocks, and the like. Materials such as wood and stone may also be used indoors, and may be subject to varying temperatures and humidity, especially in bath areas. Since most buildings and recreational facilities have a life expectancy of 10 years or more, it is an object of this invention to provide long-term (greater than 10 years) protection from algae growth for such materials.

Concrete provides durable, inexpensive building facings, roofing tiles, and statuary, but can quickly develop dark streaks due to growth of algae which, initially airborne, lands on the structure and survives thereon. Other building materials such as wood, cement, concrete, stonework, masonry, and asphalt roofing shingles likewise can become streaked by algae. The discoloration of these materials is particularly noticeable when they have a light color.

The terms "algicidal" and "algae-resistant", when referring herein to chemicals or building materials means having the capability to kill or inhibit the growth of algae commonly associated with causing discoloration of roofs and other surfaces. McMahon (U.S. Pat. No. 3,507,676) identified the dominant organism causing such discolorization on ambient atmosphere exposed building materials as the alga Gloeocapsa magma. This particular alga is capable of being transported by wind currents, and it has been shown that calcium carbonate is a macronutrient for this alga, thus it is especially vigorous on calcium-carbonate containing surfaces such as marble. Alga are unicellular or polycellular plants, and are distinguished from fungi by the presence of chlorophyll and response to photosynthesis.

Alga may cohabit with fungi on building materials and cause further coloring problems. "Lichen" comprises algae and fungi which live symbiotically, i.e., two primitive plants, one with, one without, chlorophyll, which live together. Lichens yield coloring matter (litmus, orchil, zearin), acids (e.g., orsellic acid), carbohydrates, and depsides (esterlike anhydrides of phenolcarboxylic acids).

Limestone assumes a bewildering number of widely divergent physical forms, including marble, travertine, chalk, and the like, and contains from about 55 to about 95 weight percent calcium carbonate. Individual limestone types are further described by many common names, as detailed in Kirk & Othmer, *Encyclopedia of Chemical Technology*, Third Edition, Vol..14, John Wiley & Sons (1981), pages 343–352.

Concrete, stonework, masonry, and wood can be coated with silicates or silicones (polysiloxane) coatings for water repellency, the latter such as disclosed in U.S. Pat. No. 4,877,654 (Wilson). Wilson describes aqueous emulsions useful (when applied and then cured into a polysiloxane coating) for rendering porous substrates water repellant comprising (a) a hydrolyzable silane having a predeterminable pH-stable range, (b) an emulsifying agent having an HLB value of from 2 to 20, an effective amount of (c) a buffering compound to maintain the composition within the predeterminable pH-stable range; and (d) water. It is also maintained by Wilson that such buffered compositions are stable on long term storage and maintain high effective levels of active silane content even when they include biocides which may accelerate the hydrolysis of aqueous silane-containing compositions.

Wilson is primarily concerned with water repellency of polysiloxane-coated substrates such as concrete suspended in distilled water for 21 days, as exemplified by the tests described in cols. 7 and 8, not with biocidal activity after prolonged exposure to varying ambient atmospheric conditions such as changing pH, temperature, and humidity conditions. In order to render the polysiloxane-type coatings described by Wilson resistant to unspecified organisms, Wilson notes that the uncured composition must be buffered to make the hydrolyzable silane monomers hydrolytically stable in the presence of pH shifting additives, such as biocides. However, Wilson does not disclose by way of any example that treatments with his emulsion composition (including a biocide) and subsequent polysiloxane coating were proven to render concrete resistant to algae or any other organism. Further, the coatings applied by Wilson are thick (1 liter/m$^2$), and if the concrete structure is not allowed to "breathe", it is well known that concrete structures soon deteriorate. It is undesirable to water proof such materials since they tend to crumble if they cannot breathe; thicker coatings tend to be more water proof or water resistant, and thicker coatings tend to result in higher material costs.

German Offenlegungsschrift DE 3828775 (Huttinger) describes antimicrobial compounds for controlling undesirable growth of microbes such as *E. coli* in water-bearing devices, e.g., a device containing glass microbeads for disinfecting water. In one example, glass microbeads impregnated with or coated with 3-(triethoxysilane)-ethyl-tri-n-butylstannate are tested for their ability to kill *E. coli*. In a flow through experiment, no *E. coli* was killed. However, when water was kept in contact with treated beads for one day *E. coli* were killed.

Huttinger theorizes that since the tin compounds are completely apolar, adsorption of *E. coli* did not take place, so that none were killed, but after flow interruption, the E. Coli sedimentized and were killed upon contact with the tin-silane coated glass surface.

Huttinger also disclose paper treated with one of the antimicrobial compounds and this is indicated to be useful for filtering bacteria from air.

However, from the scant information provided by Huttinger, the coating thickness or integrity cannot be determined, and the treated glass is shown to be effective against *E. coli* only when a static water sample is kept in contact with the coated beads for one day. Although a different mode of action is proposed, there is no evidence given by Huttinger that the antimicrobial compounds are not simply leaching or desorbing, in an equilibrium reaction, from the from the glass substrate. Further, there is no demonstration of effectiveness against other, more robust organisms, or against organisms in the presence of a macronutrient for that organism., and it is specifically noted that the treated glass is not effective even against *E. coli* when the aqueous medium is flowing. It is highly speculative whether the microbial action against *E. coli* could be extended to more robust organisms, such as the blue-green algae *Gloeocapsa magma*, which is transported by air-borne particles and is able to tolerate a variety of climates due to the desiccation properties of the gelatinous sheath surrounding the algae cells. Alga colonies are not known to infest glass surfaces, such as used by Huttinger.

Therefore, although compounds useful in the present invention are described in Huttinger, there is no suggestion that the compounds would be effective against established or freshly introduced alga colonies on wood, concrete, and other non-glass building materials, especially in the presence of calcium carbonate, and there is no teaching of effectiveness beyond a period of a day or a few days.

It an object of the present invention to provide a method of rendering wood, concrete, and other non-glass materials algicidal by immobilizing an algicide thereon, rather than simply compounding a biocide into a polymeric coating, which is known to provide materials which readily leach the biocide.

Tin compounds can afford fungicidal wood protection as reported in Kizlink, "Tributyltin-N N-dialkyldithiocarbamates, as Fungicides for Wood Preservation Against Rot" JOCCA Vol 74 No 9 1991 pp 329–330. The Kizlink publication also cites prior publications concerning the application of tin compounds as corrosion inhibitors, fungicides for plastics, paper, and paper pulp, and as biocides. In spite of the general effectiveness of tin compounds, however, they are sufficiently soluble in water to leach, and tin compounds are potentially toxic. So, while tin and/or tin compounds were widely incorporated into marine paints and used in other applications, it is presently undesirable to randomly select a tin compound for use in these applications, in view of greater concern for the environment and human health. To be effective against alga colonies, the algae-resistant compound and the resulting coating or treatment must be resistant to thermal, hydrolytic and photochemical degradation, under conditions far more extreme than those encountered in laboratory water or marine environments.

Algae growth on ceramic-coated roofing granules of asphalt roofing shingles can be virtually eliminated by incorporating a copper compound, such as cuprous oxide, into the ceramic coating. Such techniques are disclosed in assignee's pending patent application Ser. No. 07/945,127, filed Sept. 15, 1992. However, the cuprous oxide loadings increase the cost of manufacturing the granules, and the copper compounds readily leach out of the coating, thus diminishing their long-term effect. If copper could be incorporated into concrete, it might likewise inhibit algae growth, but copper would interfere with the setting up of the concrete, and the method is not useful for existing structures.

Applicants' previously cross-referenced patent describes and claims roofing shingles and methods of protecting same against algae streaking, the shingles comprised of roofing granules incorporating an effective amount of a compound of the general formula

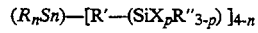

$$(R_nSn)\text{—}[R'\text{—}(SiX_pR''_{3-p})]_{4-n} \quad (I)$$

wherein

R is an organic radical of the formula $C_zH_{2z+1}$ wherein z ranges from 1 to 8, R' is a divalent radical of an aliphatic hydrocarbon containing 2 to 20 carbon atoms, R' is an organic radical containing 1 to 8 carbon atoms, X is a hydrolyzable group, n is an integer from 0 to 3, and p is an integer from 1 to 3.

Although this work is impressive, there is still a long-felt but unmet need in the art of non-particulate building materials, statuary, recreational facilities, and the like, which are exposed to changing ambient conditions (either indoors or outdoors) or other conditions conducive to algae growth, to restore or render them algae-resistant, while meeting increasing regulatory demands for low release of metals into the environment. The restoration and/or protection must be for long time periods, with little or no effects on water repellency, color, or other properties of building materials. In the absence of an adequate solution to this long-felt need, it still has been necessary to clean even water repellent concrete which is exposed to ambient environments periodically, usually with bleaches or phosphates, to remove algae growth. The cleaning operation is time-consuming and expensive and does nothing to inhibit recurring growth.

SUMMARY OF THE INVENTION

The invention concerns an economical, ecologically safe treatment that preserves or restores the aesthetic appearance of architectural and artistic structures by preventing or removing disfiguring growths such as dark streaks of green and/or black algae. The treatment not only affords such protection, but when applied to materials that are infested by algae, the streaking disappears and does not reappear.

As used herein the terms "restore" and "clean" refer not to chemical cleaning but to the restorative effect of compounds within formula (I) which results from killing of alga colonies.

Briefly, the methods of the invention involve either:

1) applying to a material to be protected or restored, and/or 2) incorporating into a material, thus forming a composite, an effective amount of a compound containing tin covalently bonded to a silylating group such that cleavage of the covalent bonds due to hydrolysis or photolysis is minimized, thus making the treatment useful for long periods of time (at least 10 years).

As used herein the term "incorporating" means that the compound is physically mixed, combined, or forced into the material to form a composite. In some embodiments the composite may be ready to use after the compound has been forced into the material, such as wood which has been pressure treated with the compound. In other embodiments, when the compound is mixed with a material, a precursor composite is formed, which may subsequently be formed into the desired shape. An example of this latter approach is when a compound as described herein is mixed with uncured concrete or cement to form a precursor composite, then the precursor composite is shape into the desired article and allowed to harden and form the final composite.

Useful compounds are of the general Formula (I):

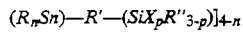

$$(R_nSn)-R'-(SiX_pR''_{3-p})]_{4-n} \quad (I)$$

wherein

R is an organic radical of the formula $C_zH_{2z+1}$ wherein z ranges from 1 to 8, preferably 3 to 6, more preferably 4;

R' is a divalent radical of an aliphatic hydrocarbon containing 2 to 20 carbon atoms, preferably 2 to 8 carbon atoms;

R" is an organic radical containing 1 to 8 carbon atoms,

X is a hydrolyzable group, preferably selected from the group consisting of halogen and alkoxy groups;

n is an integer from 0 to 3, and p is an integer from 1 to 3.

The groups R, R', R" and X may contain heteroatoms such as O or N, and they may be substituted with aryl, alkaryl or aralkyl groups. The groups R, R' and R" may contain halogen such as F, Cl or Br as long as the bonds between Sn and Si are to tetracoordinate (sp³ hybridized) carbons which are not activated by the presence of heteroatoms. Any heteroatom and any aryl, alkaryl, and aralkyl group in R" should be separated from Sn and Si by two or more carbon atoms.

Compounds within general formula (I) may be applied neat to the material to be protected, but more typically and preferably they are diluted with oil or mixed with water and formed into an emulsion, dispersion or solution. Preferred are emulsions containing from about 0.5 to about 20 weight percent of a compound within general formula (I), more preferably about 5 to 15 weight percent. The emulsion or compound is also be effective when diluted with commercially available "water proofing formulas" such as the liquid water proofing composition known under the trade designation "Thompson's Water Seal" available from Thompson & Formby, Inc. Memphis, TN, which comprises resins dispersed in petroleum distillates, the composition having a boiling range of 300–430° F. (149–221° C.). Compounds within formula (I) may be diluted with such water proofing formulas at any convenient weight ratio of compound to water proofing composition, typically from 1:99 to about 99:1, more typically from about 1:99 to about 1:1.

Specific examples of materials to be protected or "cleaned" include wood structures, particularly outdoor wood structures such as decks, patio furniture, flower boxes, shake shingles, signs and sign posts, boat docks, loading docks, stairways, playground equipment, mail boxes and supports, boat masts, and indoor wood structures such as paneling, window frames, wood flooring, especially in bathrooms or other humid indoor environments. Because algae growth on wood can retain moisture and thus cause premature decay, the novel treatment should prolong the life of wood materials.

Another class of materials which may be protected or cleaned include materials containing calcium carbonate, such as marble, concrete, and masonry. Specific examples include statues, bridges, cement shingles, sidewalks, decorative stone and brick, stucco, culverts and the like.

Yet another class of materials includes asphalt-based shingles and other asphalt-based roofing materials. These materials may be protected either by 1) coating roofing granules with an effective amount of the compound within formula (I) prior to incorporation into the shingle, 2) mixing and effective amount of the compound into the asphalt, and/or 3) coating a shingle with the compound.

Compounds of Formula (I) should be effective when applied to a material to be protected and/or cleaned in amounts as small as 0.01 gram (g) of elemental tin (effectively the same weight as a $Sn^{2+}$ or $Sn^{4+}$ ion) per square meter (m²) of building material. To ensure ecological safety, they preferably are not used in amounts greater than 0.2 g tin/m² of building material. When used within those ranges on a building material that is already infested with visible discolorization due to algae growth, several months or more than a year may elapse before the appearance is restored. When a compound of formula (I) is admixed with "filled" asphalt (i.e., asphalt having calcium carbonate or other filler therein), it is preferred to mix about 5 to 10 grams of compound per 250 lbs (about 114 kilograms) of filled asphalt. These concentrations are also be applicable to admixtures of the compounds within formula (I) with cement and concrete.

Further aspects and advantages of the methods of the invention will become apparent from the following detailed description of the invention.

DESCRIPTION OF PREFERRED EMBODIMENTS

As previously stated, compounds within general formula (I) are advantageously used in the methods of the present invention.

The R and R' groups are chosen to be chemically and photochemically unreactive and to minimize volatility and acute toxicity to mammals.

Specific examples of R include ethyl, n-propyl, iso-propyl, n-butyl, iso-butyl, sec-butyl, tert-butyl, n-pentyl, neo-pentyl, n-hexyl, n-octyl, iso-octyl, 4-(methoxy)-butyl, 4-chlorobutyl and 3,3,3-trifluoropropyl. Alkyl groups preferably are selected to minimize volatility and acute toxicity.

Specific examples of R' include ethane-1,2-diyl; propane-1,2-diyl; propane-1,3-diyl; butane-1,4-diyl; pentane-1,3,5-triyl; heptane-1,4,7-triyl; octane-1,3,5,7-tetrayl; 3-methoxypentane-1,5-diyl; 3-chloropentane-1,5-diyl; and 2-(trifluoropropyl)butane-1,4-diyl.

Specific examples of R" include methyl, ethyl, n-propyl, iso-propyl, n-butyl, iso-butyl, sec-butyl, tert-butyl, n-pentyl, neo-pentyl, n-hexyl, n-octyl, iso-octyl, 4-(methoxy)butyl, 4-chlorobutyl and 3,3,3-trifluoropropyl.

Specific examples of X include fluoro, chloro, bromo, iodo, methoxy, ethoxy, iso-propyloxy, tertbutyloxy, acetoxy and dimethylamino. Preferred is alkoxy, especially ethoxy.

Specific examples of compounds within Formula (I) include:

(n-Bu)$_3$SnCH$_2$CH$_2$Si(OEt)$_3$,
(n-Bu)$_3$SnCH$_2$CH$_2$Si (OMe)$_3$,
(n-Bu)$_2$Sn[(CH$_2$CH$_2$CH$_2$)Si(OEt)$_3$]$_2$,
(n-Bu)$_2$Sn[(CH$_2$CH$_2$CH$_2$)Si(OMe)$_3$]$_2$,
Sn[CH$_2$CH$_2$Si (OEt)$_3$]$_4$,
Sn [(CH$_2$CH$_2$CH$_2$)Si(OEt)$_3$]$_4$,
Et$_3$SnCH$_2$CH$_2$Si(OEt)$_3$,
(n-propyl)$_3$SnCH$_2$CH$_2$CH$_2$Si (OEt)$_3$,
(n-Bu)$_3$SnCH$_2$CH$_2$SiMe (OEt)$_2$ and
(n-Bu )$_3$SnCH$_2$CH$_2$SiCl$_3$, wherein "OEt" denotes the —OCH$_2$CH$_3$ radical, and "OMe" denotes the —OCH$_3$ radical.

Preferred compounds within general formula (I) are (n-Bu)$_3$SnCH$_2$CH$_2$Si (OEt)$_3$ and (n-Bu)$_2$Sn[(CH$_2$CH$_2$CH$_2$) Si(OEt)$_3$]$_2$, and most preferred is (n-Bu)$_3$SnCH$_2$CH$_2$Si (OEt)$_3$ which is herein referred to as "Formula (I-A)".

Compounds within Formula (I) have no readily hydrolyzable groups linking the tin and the silylating group. That is, the bond between the R' group and each Sn and Si atom includes tetracoordinate carbon atoms that are not activated by the presence of heteroatoms or aryl, alkaryl or aralkyl groups.

Compounds of Formula (I) preferably are prepared by either by the hydrostannylation of alkenylsilanes or by hydrosilation of alkenylstannanes. See A.G. Davies, P.J. Smith, "Tin," Chpt 11 in G Wilkinson, FGA Stone, and E.W. Abel, *Comprehensive Organometallic Chemistry*, Vol. 2, pp. 530–535, Pergamon Press: Oxford, 1982. Other methods include the reactions of organometallic reagents containing silicon such as Grignard reagents, organolithium reagents, organosodium reagents (including those formed in situ from organohalogens and sodium, the so-called Wurtz process), or organoaluminum reagents with stannyl or tin-containing organic halides, or the reactions of organometallic reagents containing tin with silyl or silicon-containing organic halides, or the acidolysis of stannylamines with silicon-containing hydrocarbon acids.

Compounds of Formula (I) may be prepared, stored, applied, and reacted with substrates neat, as solutions in organic solvents such as alcohols (including methanol, ethanol, and isopropanol), aromatic hydrocarbons (including toluene and xylene), ethers (including diethylether and tetrahydrofuran), or hydrocarbons (including hexane, cyclohexane, heptane, and octane), as water-based or oil-based emulsions, or as mixtures with polymers and optionally solvent, optionally containing various additives.

Compounds of Formula (I) may be applied to any suitable substrate by means such as spraying, dipping, rolling, painting, or brushing to the surfaces of small objects such as granules, beads, and particles or to large objects such as buildings, statues, and walls. Application may be performed in a highly controlled or controllable environment, such as laboratory or factory, or it may be performed in an environment subject to a large number of uncontrollable variables, such as an existing building, wall, statue, or other edifice. The compounds may be caused to react, via the silylating agent, with such substrates at ambient or elevated temperatures (up to 300° C.) in the presence or absence of added catalyst. Their hydrolyzable X groups should react with surface hydroxyl groups of the building materials to form Si—O—linkages. The hydrolytic stability of the bond between compounds of Formula (I) and building materials is greater at higher values of the integer p.

Compounds of Formula (I) should be effective when applied to a building material or statue in amounts as small as 0.01 g of tin per square meter of building material. To ensure ecological safety, they preferably are not used in amounts greater than 0.2 g/m$^2$ of tin. When used within those ranges on a building material that has an infestation and visible algae growth, several months or more than a year may elapse before the discolorization due to algae disappears. When compounds of Formula (I) are instead incorporated into a building material such as cement or concrete, they should be effective in amounts as small as 2 g of tin per cubic meter (m$^3$) of the material and preferably are not used in amounts exceeding 40 g tin/m$^3$.

As previously mentioned, compounds within Formula (I) are useful for protecting and/or cleaning cement tiles and wood roofing shingles. The compounds may be applied neat or in solution or emulsion, prior to or after the tiles or shingles are attached to a structure, to retard algae growth. If possible beforehand it is preferred to heat the material to be protected to at least 50° C. to enhance adhesion of the compounds to the materials, although this is not required. Preferably the materials are preheated to 100°14 125° C. Above 150° C. would be wasteful of energy, but the temperature could be as high as 250° C. without damage. It may also be preferred to prewash cement tiles and other materials with a detergent before application of the compound.

Objects and advantages of this invention are further illustrated by the following examples and test methods, but the particular materials and amounts thereof recited in these examples, as well as other and conditions and details, should not be construed to limit this invention. All parts and percentages are by weight unless otherwise specified.

Test Method

Houston, Texas Environmental Testing

Environmental testing to determine degree of discolorization due to algae growth on wood shake shingles, cement tiles, concrete walls, and asphalt shingles was carried out in Houston, TX, which is at less than 30° latitude. This latitude frequently provides daytime high ambient temperatures sometimes exceeding 100° F. (38° C.) in the summer months and ambient temperatures reaching as low as about 25° F. (−4° C.) in winter months. The region has exceptionally high humidity, having normal rainfall of about 46 inches per year, but which may be as much as 60 inches per year, with periods of heavy rain followed by long dry periods not uncommon. In addition, the pH of the roofing shingles tested varied from approximately neutral pH to acidic pH as low as 4.0. Wind gusts from thunderstorms may reach 60–80 miles per hour, and hail is not uncommon.

In the examples, the compounds tested were applied to north facing surfaces at an angle to horizontal of about 45°, since these surfaces frequently are more infested than surfaces facing other directions. This is believed to be due to the shading which occurs on north facing surfaces, particularly north facing vertical walls.

Examples

Synthesis of Compound of Formula (I-A)

In an atmosphere of dry nitrogen, 99.8 g tributyltin hydride (Lancaster Synthesis, Windham, NH, as supplied) and 71.0 g triethoxyvinylsilane (Petrarch Systems, Bristol, PA, as supplied) were mixed with 0.13 g AIBN catalyst (Aldrich Chemical Co., Milwaukee, WI, as supplied) added in three portions at 0, 3, and 6 hr reaction time. The reaction mixture was heated to 80–85° C. for a total of 23 hr. spectroscopic analysis of the mixture showed the reaction to be complete, and infrared, nuclear magnetic resonance ($^1H$ and $^{13}C$), and mass spectral analysis and elemental analysis confirmed that the product is [2-(triethoxysilyl)ethyl]-tributyltin or $(n-Bu)_3SnCH_2CH_2Si(OEt)_3$.

Example 1

After adding to water 3 drops of sodium silicate per 100 ml of water, one part of the Compound of Formula (I-A) was added per 10 parts of water to provide "Water-based Emulsion (I-A)". An identical emulsion, except substituting mineral oil for the water, is here called "Oil-based Emulsion (I-A)".

Water-based Emulsion (I-A) was applied by paint roller to a portion of a clean north-facing concrete wall, using one pint per 100 ft$^2$ (51 ml/m$^2$), i.e., 0.1 g of tin per square meter of concrete.

Results: After one year, the uncoated portion of the wall was dark colored due to algae growth whereas the coated portion of the wall was free from algae and thus not darkened.

Water-based Emulsion (I-A) was applied by paint roller to a portion of a north-facing panel having a 45° slope and bearing newly applied asphalt roofing shingles. To another portion was applied Oil-based Emulsion (I-A), each applied using one pint per 100 ft$^2$ (51 ml/$^2$), or 0.1 g/m$^2$ of tin. A portion of the panel was left uncoated by either emulsion.

Results: After four years, the uncoated portion of the asphalt shingles had algae growth whereas both coated portions remained free from algae.

Water-based Emulsion (I-A) and Oil-based Emulsion (I-A) were applied by paint roller to different portions of a north-facing panel having a 45° slope and bearing asphalt roofing shingles that had a dark algae discoloration, again applying a 0.1 g/m$^2$ of tin. Again, a portion of the panel was left uncoated.

Results: Within six months, the algae growth had disappeared from both coated portions whereas the uncoated portion retained the dark algae discoloration.

EXAMPLE 2

Roofing granules, as sold, conventionally have a mineral oil and silicone treatment which both controls dust and enhances adhesion to asphalt. To 100 parts of the mineral oil and 4 parts of the silicone was added 3 parts of the compound of Formula (I-A). Eleven parts of this modified treatment was added to an activated paint shaker containing 1000 parts of 3M roofing granules No. 93 (white) which had been pretreated to 110° C., and the shaking was continued for five minutes, thus applying ½ pint per ft$^3$ of granules or 17 g/m$^3$ of tin. After removal from the shaker, the coated granules were placed in an oven at 70° C. for one hour. These were then used in making asphalt roofing shingles from which circles 6.5 cm in diameter were cut. These circles were fitted into openings in a north-facing panel of asphalt shingles positioned at a 45° slope, which shingles were already discolored by algae.

Results: After four years, the circles were free from algae.

For comparison, circles were cut from asphalt shingles that were identical except for omission of the compound of Formula (I-A).

Results: These showed algae streaks at 18 months and became almost totally discolored by algae at four years.

EXAMPLE 3

(Acute Toxicity)

The LD 50 for $(n-Bu)_3SnCH_2CH_2Si(OEt)_3$ was determined by International Bio Research (Hannover, West Germany) in a test performed according to the "OECD Principles of Good Laboratory Practice" in *Testing of Chemicals*, OECD (Paris, France, 1982). The acute oral toxicity was investigated in one group of fasted 5 male and 5 female Wistar rats. The animals were dosed once orally by stomach tube at 5 ml/kg of body weight. No mortalities were observed in 14 days, and no abnormal macroscopic findings in the cranial, thoracic, and abdominal cavities were observed in the animals necropsied on day 14. The LD 50 was determined to be greater than 5480 mg/kg of body weight.

EXAMPLES 4–7

Four 7.5 inch×15 inch (19 cm×38 cm) cement roofing tiles were exposed on Aug. 6, 1993 on the Houston exposure deck described previously.

The tile used in Example 4 had an infestation of green algae and was coated on its lower half with Oil-based emulsion (I-A) as described above.

The tile used in Example 5 had an infestation of black algae. Before application of the tin-silane emulsion, the entire infested tile was prewashed with a detergent. The tile was then coated on its upper half with Oil-based emulsion (I-A) as described above.

The tile used in Example 6 had an infestation of black algae. This tile was not prewashed, but was coated on its upper half with Oil-based emulsion (I-A) as described above.

The tile of Example 7 was a new tile having on its upper half a coating comprising the Oil-based emulsion (I-A) as described above.

Results: The tiles of Examples 4–7 were reviewed visually on November 30, 1993 and given a rating on a 0 to 10 scale, with 0 being no visible algae growth and 10 being complete infestation. (Only treated areas of the tile were rated.)

The new tile of Example 7 showed no visible algae growth on either its coated or uncoated surface, and was rated 0.

The portion of the tile of Example 4 coated with the emulsion showed significantly reduced green algae growth as evidenced by lack of bright green algae. As some growth was still evident, the coated portion was rated 7.

The portion of the tile of Example 5 (prewashed) coated with the emulsion was clean of black algae growth as evidenced by lack of black color characteristic of that algae. This tile was rated 0.

The portion of the tile of Example 6 (not prewashed) coated with the emulsion showed significantly reduced black algae growth as evidenced by lack of black color characteristic of that algae, although slightly more than the tile of Example 5, and was thus rated 1.

Examples 8–10 and Comparative Examples A and B

A deck of 6 inch by 18 inch (15.2 cm×45.6 cm) wood shake shingles was constructed so that each shingle had an exposed area of about 6 inches×by 6 inches (15.2 cm×15.2 cm). The deck was exposed at the Houston, TX weathering facility for a period of 10 years and had developed black algae and green algae infestation. The deck consisted of 17 rows of shake shingles applied in an overlying fashion, with the shingles making up the top row of the deck partially overlying those making up the next lower row, and so on. Row 1 was the top row, and the deck was divided into five columns of shingles, each column having 17 rows and an average of about six shingles in each row. The deck and shingles had been exposed (prior to application of coatings described below) for a period of time (about 10 years) sufficient to have significant black and green algae discolorization. The shingles were originally rated 10 on Aug. 6, 1993.

The column and rows of shake shingles of Comparative Example A had no coating applied thereto on Aug. 6, 1993, while all of the coatings referred to below were applied on or shortly before that date.

For the column and rows of shake shingles of Comparative Example B, rows 8–14 had a coating of sealant known under the trade designation "Thompson's Water Seal" applied thereto, while rows 1–7 and 15–17 of this column had no coating applied thereto.

For the column and rows of shake shingles of Example 8, rows 8–12 had a coating comprising the Oil-based emulsion of Formula I-A applied thereto, while rows 1–7 and 13–17 of this column had no coating applied.

For the column and rows of shake shingles of Example 9, rows 8–14 had a coating applied thereto similar to Oil-based emulsion of Formula I-A, except it contained only 5 percent of the compound of formula I-A since the coating was formulated by adding 1 part sealant known under the trade designation "Thompson's Water Seal" to 1 part Oil-based emulsion. Rows 1–7 and 15–17 of this column had no coating applied.

For the column and rows of shake shingles of Example 10, rows 8–12 had a coating applied on Aug. 6, 1993 similar to Oil-based emulsion of Formula I-A, except it contained only 2.5 percent of the compound of formula I-A since the coating was formulated by adding 3 parts of sealant known under the trade designation "Thompson's Water Seal" to 1 part Oil-based emulsion. Rows 1–7 and 13–17 of this column had no coating applied thereto.

An exposure test was begun on Aug. 6, 1993 to determine the effectiveness of the applied coatings in cleaning up the either the black and/or green algae. The shingles were reviewed visually on Nov. 10, 1993.

Results: The shingles of Comparative Examples A and B were both rated 10. The coated shingles of Examples 8–10 showed good cleanup of green algae but still showed some black algae and were rated 7.

Thus, even after only about 3 months the infested shingles had been cleaned significantly.

Example 11 and Comparative Example C

An experiment was run to compare the algae killing ability and relative leach rates of a compound within formula (I) with cuprous oxide.

A deck of untreated three tab asphalt shingles having ceramic-coated roofing granules thereon that had been exposed at the Houston, TX weathering facility for about 5 years and thus developed black and green algae discolorization was used for Examples 11 and Comparative Example C. In one of the algae-infested shingles on the top row of shingles, two identical circular discs were cut and removed from the shingle, each disc having a diameter of about 2 inches (about 5 cm), with the resulting circular blank spaces separated by a distance of about 7 inches (about 17.8 cm).

For Example 11, a 5 cm diameter disc identical to the original shingle except for the application of a coating of the Oil-based Emulsion of Formula I-A described above was inserted into one blank space. The concentration of compound within formula (I-A) on the disc was 0.25 pounds per ton of base granules (0.13 grams per kilogram base granules).

For Comparative Example C, a disc identical to the original asphalt shingle except having 100% algicidal roofing granules (i.e. all granules were algicidal) was inserted into the other blank space. The algicidal roofing granules were identical to the non-algicidal ceramic-coated roofing granules of the original shingle except that the ceramic coating on the algicidal granules contained cuprous oxide in an amount of about 100 lbs per ton base rock (about 50 grams cuprous oxide per kilogram base rock).

Results: After a period of 6 months the shingle was viewed visually for algae reduction as determined by color change (i.e., lightening of color meant that algae was being killed). The disc of Example 11 had killed algae around the periphery of the disc only, evidence that little or none of the compound of formula (I-A) leached out from the disc. However, the area of the shingle immediately below the disc of Comparative Example C was lightened, indicating that cuprous oxide had leached out of the granules of the disc.

This test indicated that the compounds within formula (I) would be retained on the material to be protected or restored, rather than leached from the material, thus prolonging algicidal activity, while using a surprisingly low amount of algicide.

Various modifications and alterations of this invention will become apparent to those skilled in the art without departing from the scope of the following claims, and it should be understood that the claims are not to be unduly limited to the illustrative embodiments set forth herein.

What is claimed:

1. Method of protecting materials against algae streaking by applying to the material an effective amount of a compound selected from the group consisting of compounds within the general formula (I):

$$(R_nSn)-[R'-(SiX_pR''_{3-p})]_{4-n} \quad (I)$$

wherein:
R is an organic radical of the formula $C_zH_{2z+1}$ wherein z ranges from 1 to 8,
R' is a divalent radical of an aliphatic hydrocarbon containing 2 to 20 carbon atoms,
R'' is an organic radical containing 1 to 8 carbon atoms,
X is a hydrolyzable group,
n is an integer from 0 to 3, and
p is an integer from 1 to 3.

2. Method as defined in claim 1 wherein R contains from 3 to 6 carbon atoms.

3. Method as defined in claim 1 wherein R' is an alkyl group containing 2 to 8 carbon atoms.

4. Method as defined in claim 1 wherein R'' is an alkyl group.

5. Method as defined in claim 1 wherein X is a selected from halogen and alkoxy groups.

6. Method as defined in claim 5 wherein R' and R'' are alkyl groups.

7. Method as defined in claim 1 wherein n is 2 or 3.

8. Method as defined in claim 1 wherein p is 2 or 3.

9. Method as defined in claim 1 wherein the compound of the general formula (I) is (n-Bu)$_3$SnCH$_2$CH$_2$Si(OEt)$_3$.

10. Method as defined in claim 1 wherein the material is selected from the group consisting of concrete, wood, asphalt shingles, stone and masonry.

11. Method as defined in claim 1 wherein the compound of the general formula (I) is applied to the material in a water-based emulsion or an oil-based emulsion by spraying, dipping, rolling, painting, or brushing.

12. Method as defined in claim 11 wherein the compound is applied to the material in an amount providing from 0.01 to 0.2 gram of tin per m$^2$ of material.

13. Method as defined in claim 11 wherein the material has algae discoloration when the compound is being applied.

14. A composite consisting essentially of a material incorporating an effective amount of a compound selected from the group consisting of compounds within the general formula (I):

$$(R_nSn)\text{---}[R'\text{---}(SiX_pR''_{3-p})]_{4-n} \qquad (I)$$

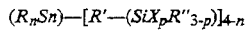

wherein

R is an organic radical of the formula $C_zH_{2z+1}$ wherein z ranges from 1 to 8, R' is a divalent radical of an aliphatic hydrocarbon containing 2 to 20 carbon atoms, R'' is an organic radical containing 1 to 8 carbon atoms, X is a hydrolyzable group, n is an integer from 0 to 3, and p is an integer from 1 to 3.

15. A composite as defined in claim 14 wherein the compound of the general Formula (I) is (n-Bu)$_3$SnCH$_2$CH$_2$Si(OEt)$_3$.

16. A composite as defined in claim 14 wherein the material is selected from concrete, wood, asphalt shingles, stone and masonry.

17. A coated material selected from wood, stone, asphalt shingles, concrete, cement and masonry having a coating thereon, the coating comprising an effective amount of a compound selected from the group consisting of compounds within the general formula (I):

$$(R_nSn)\text{---}[R'\text{---}(SiX_pR''_{3-p})]_{4-n} \qquad (I)$$

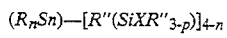

wherein

R is an organic radical of the formula $C_zH_{2z+1}$ wherein z ranges from 1 to 8, R' is a divalent radical of an aliphatic hydrocarbon containing 2 to 20 carbon atoms, R'' is an organic radical containing 1 to 8 carbon atoms, X is a hydrolyzable group, n is an integer from 0 to 3, and p is an integer from 1 to 3.

18. A coated material as defined in claim 17 wherein the compound of the general Formula (I) is (n-Bu)$_3$SnCH$_2$CH$_2$Si(OEt)$_3$.

19. A coated material as defined by claim 17 wherein said compound is present in said coating in an amount providing from 0.01 to 0.2 gram tin/m$^2$ of said coating.

20. Method of protecting calcium carbonate-containing building materials against streaking by the alga *Gloeocapsa magma* by applying to the building material an effective amount of a compound selected from the group consisting of compounds within the general formula (I):

$$(R_nSn)\text{---}[R''(SiXR''_{3-p})]_{4-n} \qquad (I)$$

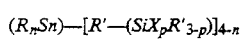

wherein

R is an organic radical of the formula $C_zH_{2z+1}$ wherein z ranges from 1 to 8, R' is a divalent radical of an aliphatic hydrocarbon containing 2 to 20 carbon atoms, R'' is an organic radical containing 1 to 8 carbon atoms, X is a hydrolyzable group, n is an integer from 0 to 3, and p is an integer from 1 to 3.

21. Method as defined in claim 20 wherein R contains from 3 to 6 carbon atoms.

22. Method as defined in claim 20 wherein R' is an alkyl group containing 2 to 8 carbon atoms.

23. Method as defined in claim 20 wherein R'' is an alkyl group.

24. Method as defined in claim 20 wherein X is a selected from halogen and alkoxy groups.

25. Method as defined in claim 20 wherein R' and R'' are alkyl groups.

26. Method as defined in claim 20 wherein n is 2 or 3.

27. Method as defined in claim 20 wherein p is 2 or 3.

28. Method as defined in claim 20 wherein the compound of the general formula (I) is (n-Bu)$_3$SnCH$_2$CH$_2$Si(OEt)$_3$.

29. Method as defined in claim 20 wherein the calcium carbonate-containing building material is selected from the group consisting of concrete, asphalt shingles, marble, stone and masonry.

30. Method as defined in claim 20 wherein the compound of the general formula (I) is applied to a finished building material from a water-based or an oil-based emulsion by spraying, dipping, rolling, painting, or brushing.

31. Method as defined in claim 30 wherein the compound is applied in an amount providing from 0.01 to 0.2 gram of tin per m$^2$ of building material.

32. Method as defined in claim 20 wherein the building material has discoloration from the alga *Gloeocapsa magma* when the compound is being applied.

33. A building material comprised of calcium carbonate and incorporating an effective amount of a compound selected from the group consisting of compounds within the general formula (I):

$$(R_nSn)\text{---}[R'\text{---}(SiX_pR''_{3-p})]_{4-n} \qquad (I)$$

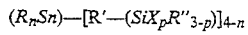

wherein

R is an organic radical of the formula $C_zH_{2z+1}$ wherein z ranges from 1 to 8, R' is a divalent radical of an aliphatic hydrocarbon containing 2 to 20 carbon atoms, R" is an organic radical containing 1 to 8 carbon atoms, X is a hydrolyzable group, n is an integer from 0 to 3, and p is an integer from 1 to 3.

34. A building material as defined in claim 33 wherein the compound of the general Formula (I) is (n-Bu)$_3$SnCH$_2$CH$_2$Si(OEt)$_3$.

35. A building material as defined by claim 33 into which the compound of the general formula (I) is incorporated as a coating in an amount providing from 0.01 to 0.2 gram tin/m$^2$ of said coating.

36. A building material as defined by claim 33 wherein an effective amount of the compound of the general formula (I) has been incorporated into material from which the building material was formed.

37. Method of protecting roofing material comprised of roofing granule-bearing shingles against algae streaking by applying to the roofing granules prior to their incorporation into shingles an effective amount of a compound of the general formula (I):

$$(R_nSn)-]R''-(SiX_pR''_{3-p})]_{4-n} \qquad (I)$$

wherein

R is an organic radical of the formula $C_zH_{2z+1}$ wherein z ranges from 1 to 8, R' is a divalent radical of an aliphatic hydrocarbon containing 2 to 20 carbon atoms, R" is an organic radical containing 2 to 20 carbon atoms, X is a hydrolyzable group, n is an integer from 0 to 3, and p is an integer from 1 to 3.

38. A roofing shingle comprised of roofing granules incorporating an effective amount of a compound of the general formula (I):

$$(R_nSn)-]R'-(SiX_pR''_{3-p})]_{4-n} \qquad (I)$$

wherein

R is an organic radical of the formula $C_zH_{2z+1}$ wherein z ranges from 1 to 8, R' is a divalent radical of an aliphatic hydrocarbon containing 2 to 20 carbon atoms, R" is an organic radical containing 2 to 20 carbon atoms, X is a hydrolyzable group, n is an integer from 0 to 3, and p is an integer from 1 to 3.

* * * * *

UNITED STATES PATENT AND TRADEMARK OFFICE
CERTIFICATE OF CORRECTION

PATENT NO.: 5,415,919      Page 1 of 2

DATED: May 16, 1995

INVENTOR(S): Billy L. George and Katherine A. Brown-Wensley

It is certified that error appears in the above-identified patent and that said Letters Patent is hereby corrected as shown below:

Col. 3, line 24-25, "organism.," should be --organism,--.

Col. 3, line 51, "N N", should be --N,N--.

Col. 3, line 53, "JOCCA Vol 74 No 9 1991" should be --JOCCA, Vol. 74, No. 9, 1991,--.

Col. 4, line 20, "formula" should be --formula (I):--.

Col. 4, line 30, "R'" should be --R"--.

Col. 5, line 25, "R'" should be --[R'--.

Col. 6, line 31, "$Sn^2$ + or $Sn^4$+" should be --$Sn^{2+}$ or $Sn^{4+}$--.

Col. 7, line 17, "($Oet_3$," should be --$(OEt)_3$,--.

Col. 8, line 34, "100° 14 125°" should be --100° - 125°--.

UNITED STATES PATENT AND TRADEMARK OFFICE
CERTIFICATE OF CORRECTION

PATENT NO. : 5,415,919
DATED : May 16, 1995
INVENTOR(S) : Billy L. George and Katherine A. Brown-Wensley It is certified that error appears in the above-indentified patent and that said Letters Patent is hereby corrected as shown below:

Col. 9, line 41, "ml/$^2$" should be --ml/m$^2$--.
Col. 13,
Claim 17, line 6, "R"" should be --R"--.
Col. 14,
Claim 20, line 7, "R'" should be --R'--.
Col. 15,
Claim 37, line 6, "R'" should be --R'--.

Signed and Sealed this

Nineteenth Day of August, 1997

*Attest:*

BRUCE LEHMAN

*Attesting Officer*   Commissioner of Patents and Trademarks